US007235382B2

(12) United States Patent
Endo et al.

(10) Patent No.: US 7,235,382 B2
(45) Date of Patent: *Jun. 26, 2007

(54) PREPARATION CONTAINING CELL EXTRACTS FOR CELL-FREE PROTEIN SYNTHESIS AND MEANS FOR SYNTHESIZING PROTEIN USING THE PREPARATION

(75) Inventors: Yaeta Endo, Matsuyama (JP); Shigemichi Nishikawa, Kusatsu (JP)

(73) Assignee: CellFree Sciences Co., Ltd., Kanagawa (JP)

( * ) Notice: Subject to any disclaimer, the term of this patent is extended or adjusted under 35 U.S.C. 154(b) by 0 days.

This patent is subject to a terminal disclaimer.

(21) Appl. No.: 11/089,652

(22) Filed: Mar. 25, 2005

(65) Prior Publication Data

US 2005/0186655 A1 Aug. 25, 2005

Related U.S. Application Data

(62) Division of application No. 10/019,995, filed as application No. PCT/JP99/04088 on Jul. 29, 1999, now Pat. No. 6,905,843.

(30) Foreign Application Priority Data

| May 11, 1999 | (JP) | ............................ 11/130393 |
| May 11, 1999 | (JP) | ............................ 11/130395 |
| May 31, 1999 | (JP) | ............................ 11/151599 |

(51) Int. Cl.
  *C12P 21/00* (2006.01)
  *C12N 15/09* (2006.01)

(52) U.S. Cl. .................. 435/69.1; 435/419; 435/430.1; 435/252.1; 435/283.1; 435/286.5; 530/350

(58) Field of Classification Search ............. 435/430.1, 435/69.1, 419, 252.1, 283.1, 286.5; 530/350
See application file for complete search history.

(56) References Cited

U.S. PATENT DOCUMENTS 6,905,843 B1 * 6/2005 Endo et al. ................ 435/69.1

FOREIGN PATENT DOCUMENTS

| JP | 07-203984 | 8/1995 |
| JP | 10-080295 | 3/1998 |
| WO | WO 98/02532 | 1/1998 |

OTHER PUBLICATIONS

Supplementary Partial European Search Report for EP 99 93 3168 dated Jul. 23, 2004.
Gaitero et al., "Purification of a Novel Heat-Stable Translational Inhibitor from Rabbit Reticulocyte Lysates," Federation of European Biochemical Societies Letters, vol. 236, No. 2, 1998, p. 479-483.
Mendez et al., "Primary Structure of ω-Hordothionin, a Member of a Novel Family of Thionins from Barley Endosperm, and Its Inhibition of Protein Synthesis in Eukaryotic and Prokaryotic Cell-Free Systems," European Jounal of Biochemistry, vol. 239, 1996, p. 67-73.
Kigawa et al., "Cell-Free Production and Stable-Isotope Labeling of Milligram Quantities of Proteins," Federation of European Biochemical Societies, vol. 442, 1999, p. 15-19.
Madin et al., "A Highly Efficient and Robust Cell-Free Protein Synthesis System Prepared from Wheat Embryos: Plants Apparently Contain a Suicide System Directed at Ribosomes," PNAS, vol. 97, Jan. 18, 2000, p. 559-564.
Endo, Y. et al., J. Biol. Chem., vol. 262, No. 12, Apr. 1987, pp. 5908-5912.
Yoshinari, S. et al., Eur. J. Biochem., vol. 242, 1996 (no month), pp. 585-591.
Peattie, D., Proc. Nat'l Acad. Sci. USA, vol. 76, No. 4, Apr. 1979, pp. 1760-1764.
Endo, Y. et al., J. Biol. Chem., vol. 258, No. 4, Feb. 1983, pp. 2662-2667.

* cited by examiner

*Primary Examiner*—Chih-Min Kam
(74) *Attorney, Agent, or Firm*—Kilyk & Bowersox, P.L.L.C.

(57) ABSTRACT

Disclosed are a preparation containing cell extracts for cell-free protein synthesis, prepared by excluding from a living organism a system, participating to inhibiting of self protein synthesis reaction, an apparatus for cell-free protein synthesis reaction equipped with a reaction tank for cell-free protein synthesis, and a kit for use therefor; the preparation can be stored at room temperature and prepared as a preparation in a state where biological functions of the cell extracts are maintained, and further, disclosed is methods for cell-free protein synthesis comprising providing cell extracts from which an inhibitor for self protein synthesis reaction is substantially excluded, having introduced therein treatment selected from supplement, storage, exchange or discharge with respect to an element selected from at least mRNA serving as a template for synthesis reaction, an energy reproduction system enzyme, a substrate, and an energy source.

11 Claims, 9 Drawing Sheets

(A)

0  10  20  30  40  50  60  ↑
Reaction time (hour)

Dihydrofolate reductase standard product (B)

10  20  30  60
Reaction time (hour)

(C)

PREPARATION CONTAINING CELL EXTRACTS FOR CELL-FREE PROTEIN SYNTHESIS AND MEANS FOR SYNTHESIZING PROTEIN USING THE PREPARATION

The present application is a divisional application of U.S. patent application Ser. No. 10/019,995, with a §371 date of Nov. 20, 2001 now U.S. Pat. No. 6.905.843 B1, which is a National Stage entry of International Application No. PCT/JP99/04088 filed Jul. 29, 1999, which in turn claim priority to Japanese Patent Application Nos. 11-130393 filed May 11, 1999, 11-130395 filed May 11, 1999, and 11-151599 filed May 31, 1999.

TECHNICAL FIELD OF THE INVENTION

The present invention relates to a preparation containing a cell extracts for cell-free protein synthesis prepared from cells and tissues for use in cell-free protein synthesis system, the preparation obtained by stabilizing thereof, enabling of storing and transporting at room temperature, and means and apparatus for synthesizing the cell-free protein using the same.

BACKGROUND OF THE INVENTION

Protein synthesizing reactions which occur in cells proceed in a process to synthesize the protein in which first from DNA having genetic information, the information is transcribed to mRNA and ribosomes translate said information of mRNA. Currently, as the method for performing ex vivo protein synthesis, e.g., in vitro, there has been intensively conducted investigation on a cell-free protein synthesizing method in which ribosomes are extracted from a living organism and in vitro protein synthesis is performed using thereof (Japanese Patent Laid-open Publication Nos. Hei 6-98790, Hei 6-225783, Hei 7-194, Hei 9-291, and Hei 7-147992). In this method, *Escherichia coli*, embryo, rabbit reticulocyte, etc. have been used as a raw material of ribosome.

Cell-free protein synthesizing reaction mixture containing cell extracts for use in cell-free protein synthesizing system and chemical substances which are indispensable for or increases an efficiency of translation reaction, such as other synthetic substrates excluding translation temperate, energy sources and various ions, and etc. are instable at an ordinary temperature and their stable storage has been merely possible at a super low temperature of −80° C. or lower.

Cell-free protein synthesizing system is a useful method which is capable of retaining accurate performances, comparable to living cells in a peptide synthesis reaction rate and translation reaction and obtaining target protein without practicing complicated purification step. Therefore, to more usefully apply the synthesizing system in industry, several inventions relating to an improvement in synthesizing efficiency has been published. However, in order to improve the usefulness in industry, it is necessary to provide not only synthesizing efficiency but also various substances used in the synthesizing system with stably retaining and supplying in high quality.

An object of the present invention is to provide a means capable of being stable in an ordinary temperature and maintaining biological function of the preparation containing a cell extracts for cell-free protein synthesis containing cell extracts for cell-free protein synthesis necessary for cell-free protein synthesizing system, and chemical substances, which is indispensable for or increases the efficiency of the translation reaction, such as other synthesizing substrates excluding translation templates, energy sources, and various ions, etc.

Another object of the present invention is to provide a means for stably storing and supplying a kit comprising a preparation containing cell extracts for cell-free protein synthesis, thereby simplifying operation steps in cell-free protein synthesis.

Still another object of the present invention is to provide a means for cell-free protein synthesis using a preparation containing cell extracts for cell-free protein synthesis, which is improved in productivity, yield, and simplicity.

SUMMARY OF THE INVENTION

The inventors of the present invention have made intensive investigation to solve above objects and, as a result, the inventors completed the present invention by, as one of means, excluding a system participating in inhibiting protein synthesis reaction, per se, in cells for cell-free protein synthesis as a raw material. Another means of the present invention includes application of a treatment such as freeze-drying cell extracts prepared for cell-free protein synthesis, or cell extracts for cell-free protein synthesis and substances participating in cell-free protein synthesizing reaction system, to prepare a dry preparation thereby completing the present invention.

Further, still another means of the present invention includes, as a cell-free protein synthesizing method using cell-free protein synthesizing system obtained by the above means, provision of cell-free protein synthesis means applying a principle of molecular sieving.

Yet another cell-free protein synthesis means is a continuous cell-free protein synthesizing means with applying a dialysis membrane and relates to additional introduction of selected elements and to apparatus therefor.

BRIEF DESCRIPTION OF THE DRAWINGS

In FIG. 4A, the left-side Lane represents molecular weight markers of 94 kDa, 67 kDa, 43 kDa, 30 kDa, and 20.1 kDa, respectively, from top. Arrows indicate synthesized dihydrofolate reductase.

In FIGS. 5 and 6, each symbol has the following meaning.
1 Impregnation tank
2 Lid portion
3 Dialysis external liquid
4 Liquid level of dialysis external liquid
5 Inlet for supplying substrate and/or energy source, etc.
6 Outlet in the impregnation tank for supplying substrate and/or energy source, etc.
7 Channel
8 Inlet in an impregnation tank for discharging a dialysis external liquid
9 External discharge outlet for discharging a dialysis external liquid
9a External discharge outlet for discharging a dialysis external liquid
10 Channel
11 Inlet for supplying mRNA and/or energy reproduction system enzyme
12 Medium having a function of dialysis membrane
13 Introductory part for Inlet 11
14 Jig for holding a membrane
15 End portion of a membrane
16 Magnetic stirrer
17 Introductory part for inlet 5
18 Introductory part for outlet 6 in an impregnation tank
19 Introductory part for inlet 8 in an impregnation tank
20 Introductory part for external discharge outlet 9
20a Introductory part for external discharge outlet 9a FIG. 7 shows maintenance of the effect of protein synthesis by supplemental addition of mRNA and creatine kinase. In the figure, ○-○ indicates supplemental addition of mRNA coding for dihydrofolate reductase with a CAP and creatine kinase, △-△ indicates supplemental addition of mRNA only, ▽-▽ indicates supplemental addition of creatine kinase only, □-□ indicates no supplemental addition, and arrows indicate timing of supplemental addition.

BEST MODE FOR CARRYING OUT THE INVENTION

Figure 1:
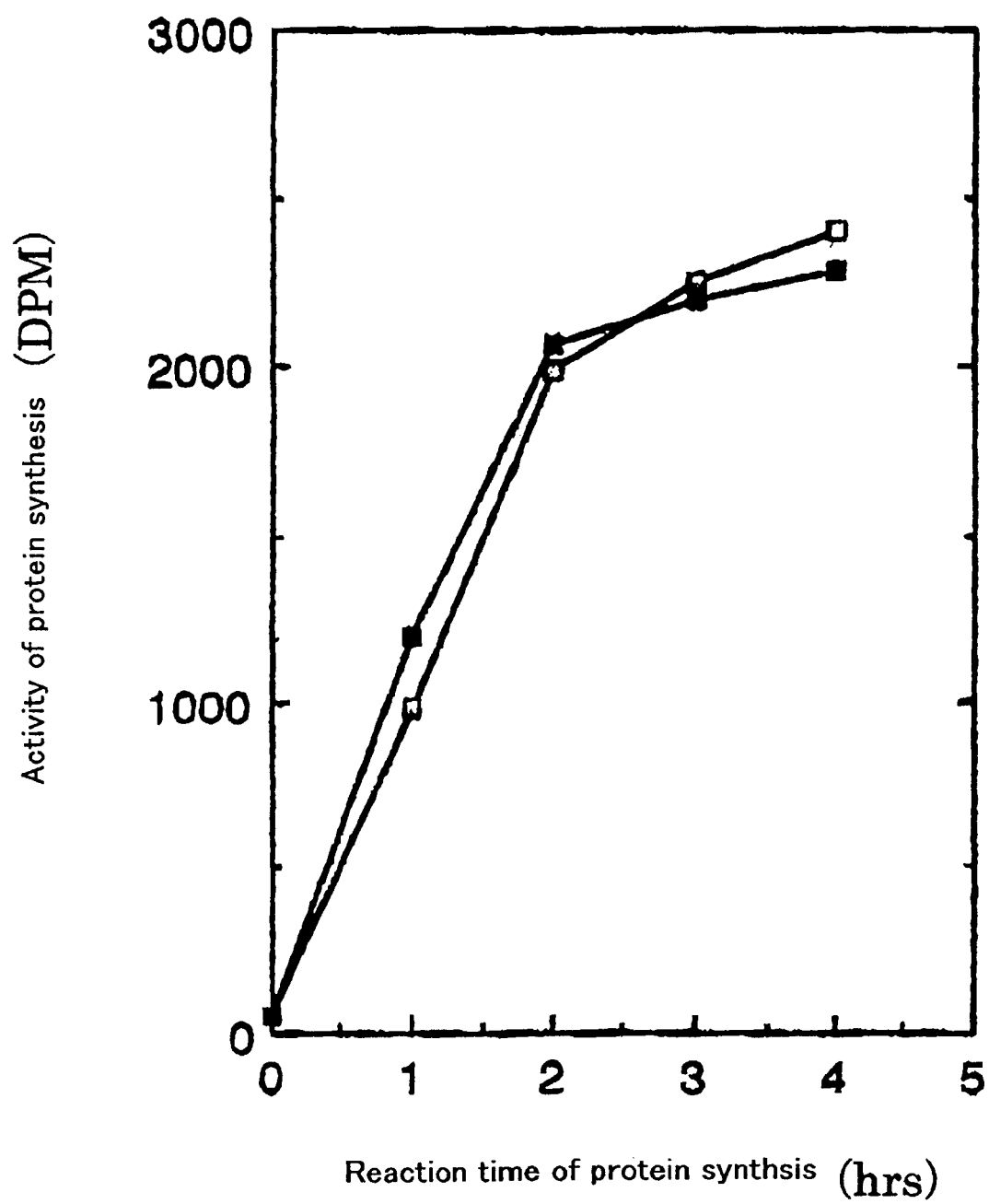
FIG. 1 shows protein synthesis activity in which freeze-dried wheat germ extract stored at −80° C. for 2 months comparing with non-freeze-dried wheat germ extract stored in liquid nitrogen for 2 months. In the figure, symbols indicate extract stored in liquid nitrogen for 2 months according to a conventional method as (□-□) and one stored for the same period of time after freeze-drying as (■-■), respectively, and ordinate represents radioactivity incorporated in protein (DPM/5 µl of reaction mixture) and abscea represents reaction time at 26° C.

1) Exclusion of a System Participating in Inhibition of Own Protein Synthesizing Reaction in Cell for Cell-Free Protein Synthesis Exclusion of a system participating in inhibition of own protein synthesizing reaction in cell, as a raw material, for cell-free protein synthesis, as one of means of the present invention, signifies a removal of means for controlling the synthesis of the own protein that the raw material cells themselves contain or hold therein. In particular, exclusion of the participating system that the present inventors have found, signifies an exclusion of substances, which act on ribosome, translation protein factors, mRNA, and tRNA, and inhibit the functions thereof.

The substances contained or held by raw material cells that suppress the function for protein synthesis include tritin (Massiah, A. J., and Hartely, M. R. (1995) Planta, 197, 633-640), protein called thionine that contains much cystein (Brummer, J., Thole, H. and Kloppstech, K. (1994) Eur. J. Biochem, 219, 425-433), ribonuclease (Matsushita S., Mem. Res. Inst. Food Sci. Kyoto Univ., No. 19, 1-), and the like, which have been known to be abundantly localized in, for example, an albumen of a seed.

By completely excluding from a germ specimen a group of cell-free germ protein synthesis suppressing (inhibiting) proteins localized in albumen contaminating in the step of isolating germ, e.g., tritin, thionine, ribonuclease, etc., inactivation reaction in protein synthesis can be canceled.

That is, one of the means of the present invention can be achieved by a technology for removing self protein synthesizing reaction suppressing mechanism that operates when a tissue of a living organism or cells are injured, that is, self protein synthesizing reaction destructing mechanism as an anti-pathogen self defensive mechanism physiologically furnished, and a technology for neutralizing or removing protein synthesis reaction suppressing activity that is induced upon the destruction, and the preparation of extracts for cell-free protein synthesis from cells or tissue.

As the raw material cell of the present invention, there can be basically used germs, *Escherichia coli*, reticulocytes, cancer cells, etc., which are used generally in cell-free protein synthesizing systems, and in addition, cells for cell-free protein synthesis originating from other organisms. In a preferred embodiment, the raw material cell includes germs originating, for example, wheat, barley, rice plant, corn, spinach, buckwheat, and etc.

Preparation of cell extracts for cell-free protein synthesis of the present invention from these raw material cells may be performed in combination with various known methods (Johnston, F. B. et al. (1957) Nature, 179, 160-161). The means useful for removing the means for controlling in synthesis of self proteins, which is one of the present inventions, is to treat the raw material cells with a surfactant, in particular a nonionic surfactant. A wide variety of nonionic surfactants may be used so far as it is a nonionic. Preferred examples thereof include Brij, Triton, Nonidet P-40, Tween, and the like, which are polyoxyethylene derivatives. Among them, Nonidet P-40 is the most preferred. These nonionic surfactants are used in a concentration of, for example, 0.5%.

When wheat germ, for example, is used as raw material cell, the treatment is to recover germ extracts by steps for milling, floatating and sieving using known means. The germ extracts are washed with a surfactant several times in order to exclude the albumen portion which has contaminated therein. This is performed until the washings are not turbid. The treatment is carried out preferably in combination with ultrasonication, which gives rise to a more complete effect.

The germ extracts, thus obtained, are substantially completely free from albumen that contains an endogenous specific inhibitor, such as tritin, and etc., and the germ has been purified substantially. Upon assaying the contamination of albumen proteins before and after the ultrasonication by an immunoblot method using an anti-tritin antibody and tritin as an index, it has been confirmed that ultrasonication washing resulted in reducing in tritin content to below detective limit. This indicates that the germ extracts is substantially free from contamination with albumen proteins and that other protein synthesis inactivating factors localized in albumen, such as thionine and ribonuclease, are also removed from the germ extracts. The obtained germ extracts are purified to such an extent that ribosomes are not deadenylated substantially, and the ribosome deadenylation ratio is below 7%, preferably 1% or less.

2) Means for Stabilizing Preparation

Another means of the present invention is to introduce for stabilizing means preparation for the thus-prepared cell extracts for cell-free protein synthesis. Hitherto, the method for storing the cell extracts for cell-free protein synthesis is to store in the vicinity of −80 to −196° C., while by introducing the means, a preparation containing the cell extracts for cell-free protein synthesis can be stored stably at room temperature. Achievement of the technology in which the preparation of the present invention can be stored at room temperature, is useful in industry.

The means for stabilizing the cell extracts for cell-free protein synthesis is to form a preparation by means of dry process, in particular by means of freeze-drying. The freeze-drying may be performed by using a method known, per se. For example, the cell extracts for cell-free protein synthesis are quickly frozen with liquid nitrogen. The drying is performed for 3 hours using a conventional freeze-drying apparatus. After completion of the removal of water, the obtained powdery preparation is sealed under vacuum or nitrogen atmosphere, thus being capable of formating into the preparation.

The above preparation may be formed with only the cell extracts for cell-free protein synthesis that have been treated by the means of the present invention, but if desired, may be formed into a preparation after selection and addition of substances essential in the cell-free protein synthesizing system, for example, synthesized substrates, amino acids or energy sources.

To the above preparation may be added substances which increases the reaction efficiency of cell-free protein synthesizing system, for example, various ionic compounds, preferably potassium ion compound, magnesium ion compound, etc.

Further, to the preparation may, if desired, be added substances which enhances solubility, for example, surfactants, substances which protects the above ribosomes from deadenylation thereof.

More preferably, the preparation is adjusted to a composition which may achieve optimization of the reaction by merely adding water. The composition may be used by forming a kit of the preparation and mixing thereof on demand. Of course, in the formation of a kit, cell extracts for cell-free protein synthesis alone, substances essential to cell-free protein synthesizing system, substances which increase the reaction efficiency of cell-free protein synthesizing system, and further aqueous solution suitable for the optimization of the reaction, etc. may be selected for forming the kit.

3) (Means for Cell-Free Protein Synthesis: Utilization of a Molecular Sieve Carrier)

In another embodiment of the present invention, a reaction tank for use in cell-free protein synthesis systems may be prepared with a carrier capable of molecular sieving. The carrier is not limited, particularly so long as it is suitable for a fractionation molecular weight of 10,000 or less. The carrier material includes, for example, porous gel filtration particles, more specifically Sephadex G10 to G25, etc. The carrier may be adjusted with water. More preferably the carrier is equilibrated with a buffer solution before use. The carrier may be adjusted after filling in a reaction tank or may be formed into a kit separately from the reaction tank, so that it may be adjusted on demand.

The reaction tank is preferably one which allows chromatography, more preferably column chromatography. The column diameter, column length, and carrier volume can be adjusted appropriately by combination of reaction time and developing speed. The volume of reaction tank can be selected appropriately depending on an amount of synthesis of target protein. The suitable reaction tank is one having at least two openings that can be opened when needed, so that a carrier may be filled in advance and is adjusted so that raw material substances participating in the cell-free protein synthesis system may be dispersed therein, if desired.

The filling of the carrier in the reaction tank is possible when needed or in advance. It is desirable that the raw material substances participating in the cell-free protein synthesizing system, in particular synthesis substrates, for example, amino acids, energy sources, including ATP, GTP, creatine phosphate, and ionic components that increase the efficiency for cell-free protein synthesizing reaction that are added, if desired, be dispersed uniformly in the filled carrier, more preferably in an optimum dispersion state, particularly in a localized uniform dispersion. The dispersion state is attained with calculating reaction efficiency in taking consideration of an association of development of these substances in the mobile phase of the carrier and of a development speed of the cell extracts for cell-free protein synthesis and/or translation template substance, separately filled.

Here, if desired, the carrier may be exclusively constituted with a molecular sieve carrier and separately a preparation which is prepared in advance with appropriately selected cell extracts for cell-free protein synthesis, synthesis substrates, energy sources, and if desired, ionic components that increase the efficiency for cell-free protein synthesizing reaction, is filled into the carrier on demand, and a translation template substance is filled and developed, thereby performing the cell-free protein synthesis.

The development speed of a mobile phase in the carrier capable of molecular sieving depends, on the size of a column and synthesis efficiency, but generally, the speed ranges from 1/10 to 1/30 of an inner volume of the column per hour. The solution used for development is a solution which contains a synthesis substrate, for example, amino acid, an energy source including ATP, GTP and creatine phosphate, and ionic components optionally added to increase the efficiency for cell-free protein synthesizing reaction, but it is not limited thereto. The development is preferably controlled automatically but it is not limited thereto.

The synthesizing reaction is preferably carried out in a reaction tank filled with the carrier. However, in consideration of the filling conditions, the reaction may be conducted in the carrier supernatant, or may be started in a batch, further followed by synthesizing the reaction during carrier development.

The synthesis reaction of the present invention is characterized in that the cell extracts for cell-free protein synthesis, such as ribosomes, move as a mobile phase, and by-products generated in the synthesizing reaction are separated and removed by fractionation-wise development, and that at the same time, the synthesis proceeds at the maximum reaction rate under supplying chemical substances which are indispensable for translation reaction, or for increasing the reaction efficiency, such as synthesis substrates, energy sources, and various ions at optimum concentrations.

The means of the present invention can be practiced by automatically controlled filling and developing material substances participating in cell-free protein synthesis system and recovering synthesized protein. The automation may be controlled by every process unit, if desired. More preferably, the solution development speed in mobile phase is automatically controlled.

The means of the present invention can continuously recover a large amount of protein in a high purity by a linkage of purification means known per se, such as various ion exchange columns or affinity columns, and etc., depending on the target protein.

Thus, by use of the means of the present invention explained above, a method for efficiently producing the target protein can be provided.

Further, by use of the means of the present invention explained above, an apparatus for the target cell-free protein synthesis can be provided.

In addition, by use of the means of the present invention explained above, a kit comprising a set suitable for the target cell-free protein synthesis can be provided.

4) Means for Continuous Cell-free Protein Synthesis (Supplemental Addition of Each Element)

In another embodiment, the present invention can be achieved by supplemental addition of each element for use in cell-free protein synthesis system.

In the present invention, mRNA serving as a template for synthesis reaction is supplemented on demand or continuously after initiating the reaction, at around a time for appearing a tendency in which the template activity of mRNA added as a raw material decreases. The addition may be made on demand in a very small amount continually, or periodically. The addition amount is an order of from one tenth to equivalent to the amount of raw material mRNA. The feature of the present invention is that the effect of supplemental addition has been confirmed for the first time and the addition amount and timing can be readily changed or fixed by those skilled in the art with confirming the effect of synthesis. The same is true for other elements and in the same sense, even if there will be no specific description hereinbelow.

In the present invention, an enzyme in an energy reproduction system is supplemented on demand or continuously after initiating the reaction, at around a time for appearing a tendency, in which the activity of energy reproduction system enzyme added as a raw material decreases. The addition may be made in a very small amount continually or periodically. The addition amount is an order of from one tenth to equivalent to the amount of raw material energy reproduction system enzyme. The energy reproduction system enzyme is suitably creatine kinase. Of course, substances having similar function to that of the present invention can similarly be added as an enzyme for an energy reproduction system. The addition amount and method therefor can be changed on demand, with referring to the amount of synthesis, as a marker.

The supplemental additions of mRNA and the enzyme for the energy reproduction system may be performed separately each other, but may preferably be made in combination. The addition method may be either continuously or intermittently. The addition amount and the method therefor may be changed on demand with referring to the amount of synthesis, as a marker.

In the present invention, in addition to the supplemental addition of mRNA and/or the supplemental addition of enzyme for energy reproduction system, a step for preventing the exhaustion of substrate and/or, energy source and/or a step for discharging by-products can be accompanied. It is preferred that various amino acids, ATP, GTP, etc. are supplementally added as a substrate or energy source continuously or intermittently. The addition amounts thereof are preferably maintained at concentrations of respective substances at the time for initiating synthesis or at concentrations close thereto. However, the addition amounts may be supplemented or changed when needed using the effect of synthesis as a marker.

A discharge of the by-products means discharging metabolites such as AMP and GMP, etc., and reaction products, such as phosphoric acid and pyrophosphoric acid, etc., and such compounds are preferably discharged from the reaction system continuously or intermittently.

As steps for preventing the exhaustion of substrate and/or energy source, and/or steps for discharging by-products are/is preferably continuous or intermittent renewal of the reaction medium in the reaction system. In the present invention, for example, a method in which a dialysis membrane is used is cited. In this case, for example, a dialysis external liquid is continuously or intermittently renewed or exchanged.

The supplement, storage, exchange or discharge of each element are treated preferably in automation. The means for automation is to provide an apparatus under a control of computer system known, per se., and performs the supplement, storage, exchange or discharge of each element integrally. Reagents for use in these steps as respective elements are preferably prepared in the form of a kit.

5) Apparatus for Automatic Continuous Cell-Free Protein Synthesis

An apparatus for automatic cell-free protein synthesis is under a control of computer system known, per se., and has, in combination, a function for setting up an environment optimal for protein synthesis, in addition to the function for integrally performing the supplement, storage, exchange or discharging of each element.

That is, a plurality of dialysis vessels can be set at a desired temperature by placing, for example, in a plurality of chambers independent of each other, each equipped with an electronic cooling apparatus and a heater and being capable of varying temperature ranging from 15 to 37° C., thereby being capable of maintaining the optimal temperature for the synthesis of the target protein.

As the method for continuously or intermittently renewing or exchanging the dialysis external liquid in a dialysis vessel, the rate of renewal or exchange of dialysis external liquid can be varied between 0.1 and 1 ml/hour, for example, by use of a dispensing apparatus such as a peristaltic pump or a syringe pump, etc., continuously or intermittently to thereby select optimal conditions for the synthesis of the target protein.

Further, substances necessary for the protein synthesis, such as template mRNA and creatine kinase, an energy reproduction system enzyme, etc., may be supplementally added in a desired amount to a protein synthesizing reaction system portion placed in the plurality of dialysis vessels for every desired times, for example, at an interval of 6 to 15 hours.

In the above apparatus, respective elements such as template mRNA, a substrate for an energy reproduction system enzyme, an energy source, a dialysis external liquid, etc., are stored individually or in admixture in storage vessels connected to dialysis vessels, respectively, and supplied through respective passages that connect the storage vessels to the protein synthesizing reaction system portions or dialysis vessels. The storage vessels are maintained preferably at 4° C.

6) Constitution of an Apparatus for Continuous Cell-Free Protein Synthesis

As an example of an apparatus for use in a continuous cell-free protein synthesis system for embodying the present invention, a cartridge apparatus will be explained. However, the apparatus of the present invention does not have to be of a cartridge type.

The cartridge apparatus is an apparatus for continuous cell-free protein synthesis having a constitution comprising an impregnation tank which is generally of a hollow body with a bottom and lid portion fitted thereto tightly sealably. This apparatus carries a passage having an inlet as means for introducing a substrate and/or an energy source and an outlet communicating with a liquid chamber in the impregnation tank for the dialysis external liquid, a passage having an inlet existing in the liquid chamber in the impregnation tank, whose inlet is as means for discharging metabolites, etc. in the dialysis external liquid and an outlet communicating with outside, an inlet as means for introducing mRNA and/or an energy reproduction system enzyme, and a medium having the function of a dialysis membrane existing in the liquid chamber in the impregnation tank for the dialysis external liquid. Hereafter, the cartridge of the present invention will be described in detail referring to the drawings. However, the apparatus shown in the drawings is a mere embodiment and the present invention is not limited thereto.

Figure 5:
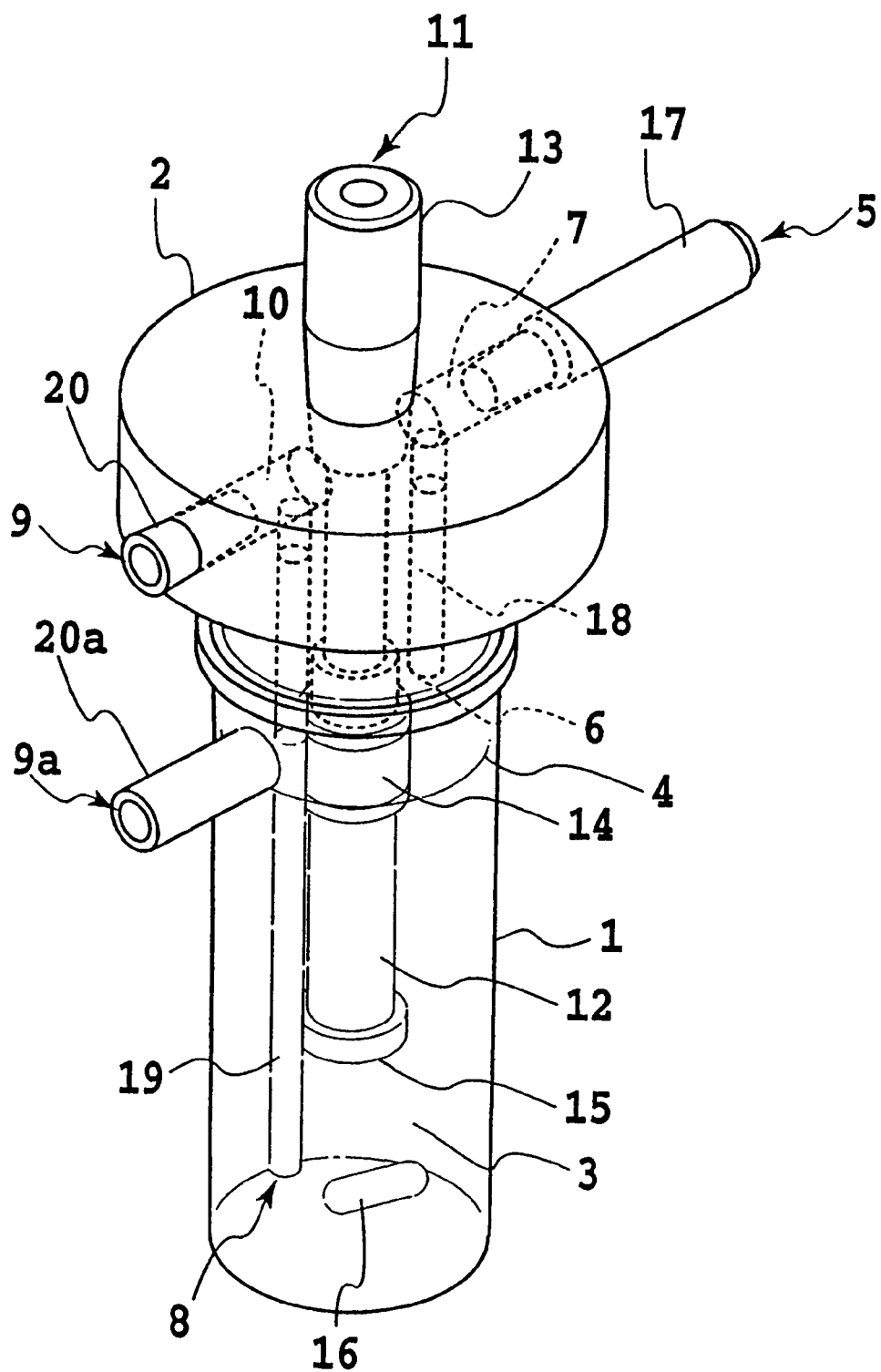
FIG. 5 is a perspective view showing a cartridge apparatus.
Figure 6:
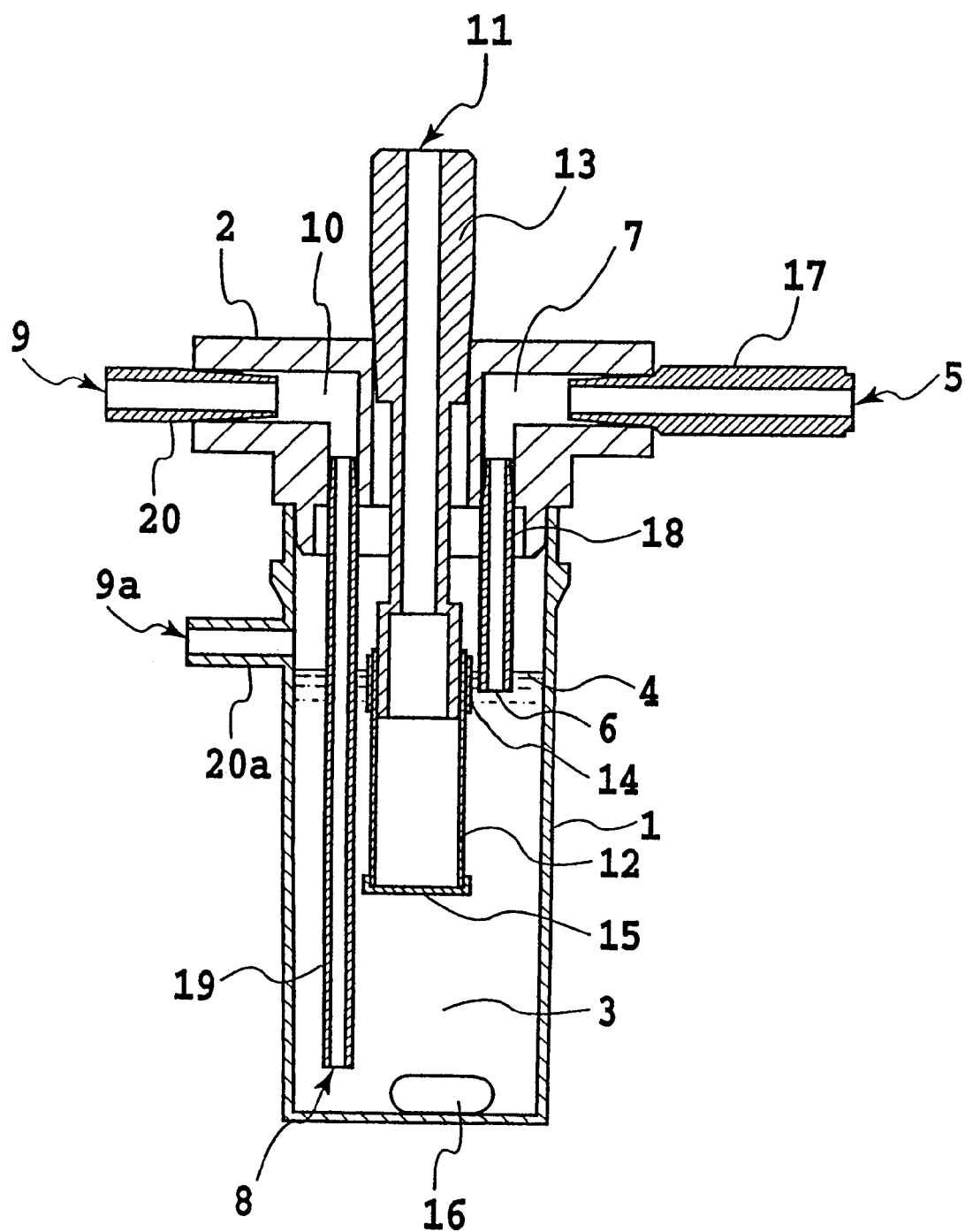
FIG. 6 is a central cross-sectional view showing a cartridge apparatus.

The cartridge apparatus includes an impregnation tank 1, which is of a generally hollow body with a bottom, and a lid portion 2 fitted thereto tightly and sealably and a dialysis external liquid 3 is filled in the impregnation tank 1 up to a level 4. More specifically, the apparatus carries as a fundamental constitution a passage 7 having an inlet 5 as means for introducing an energy source, etc. and an outlet 6 communicating with a liquid chamber in the impregnation tank 1 for the dialysis external liquid 3, a passage 10 having an inlet 8 existing in the liquid chamber in the impregnation tank 1, whose inlet is as means for discharging metabolites, etc. in the dialysis external liquid 3 and an outlet 9 and/or 9a communicating with the outside, and an inlet 11 as means for introducing substances for the synthesis system, and a medium 12 having the function of a dialysis membrane existing in the liquid chamber in the impregnation tank 1 for the dialysis external liquid 3. As an embodiment, FIGS. 5 and 6 show a cartridge apparatus whose impregnation tank is of a cylindrical body. However, the shape of impregnation tank is not limited to a cylindrical body.

Here, the outlet 6 communicates with the dialysis external liquid 3 in the liquid and an end portion of the outlet 6 is positioned in the upper half of the impregnation tank 1 and at least below the liquid level 4. The inlet 8 communicates with the dialysis external liquid 3 in the liquid and an end portion of the inlet 8 is positioned in the lower half of the impregnation tank 1. The position of the end portion of the outlet 6 and the position of the end portion of the inlet 8 may be upside down.

The outlet 9a and the introductory part 20a contact with the liquid level 4 at the same site and are positioned at an upper position than the liquid level 4. The outlet 9a and the introductory part 20a together enable discharge by spontaneous flowing out. In the case where discharge of the metabolites, etc. in the dialysis external liquid 3 is performed through the outlet 9 and the introductory part 20, the outlet 9a and the introductory part 20a may be closed or the impregnation tank molded without the outlet 9a and the introductory part 20a at the time of molding may be used. In the case where the discharge of the metabolites, etc. in the dialysis external liquid 3 is performed by spontaneous discharge through the outlet 9a and the introductory part 20a, the outlet 9 and the introductory part 20 may be closed or the impregnation tank molded without the outlet 9 and the introductory part 20 at the time of molding may be used. In this case, though not shown, the introductory part 19 and the introductory part 20a may be molded and used so that the introductory part 20a of the outlet 9a and the introductory part 19 of the inlet 8 can be connected to each other. Upon the molding, the end of introductory part 19 of the inlet 8 on the side of the outlet 9 is not connected to the lid portion but is connectable to the introductory part 20a of the outlet 9a.

The medium 12 having the function of a dialysis membrane may be molded integrally with an introductory part 13 of the inlet 11 or fixed thereto by means of a jig 14 (Jig for holding a membrane) for holding the membrane as illustrated. The medium 12 is arranged in the impregnation tank 1 in such a position that it is immersed in the dialysis external liquid 3. The end opposite to the direction for connecting to the inlet 11 of the medium 12 may be arranged in the impregnation tank 1 in such a position that it is immersed in the dialysis external liquid 3 and it is sufficient if it is closed. As a specific example thereof, it may be closed a lid-like member such as a membrane end portion 15 or the medium 12 may be of a bag-like structure having only one opening.

The cartridge apparatus may preferably have means for stirring the dialysis external liquid 3. As a specific example, a rotary medium such as a magnetic stirrer 16 may be placed in the impregnation tank 1.

The impregnation tank 1 is preferably made homeostatic for the synthesis efficiency and may be used in combination with a desired homeostatic means. For example, the impregnation tank 1 may be adjusted so that it can be arranged in an incubation tank. The cartridge apparatus is provided to users usually in a state where the dialysis external liquid 3 and synthesis system substances are not immersed and users flow the liquid through the inlet 11 and the inlet 5 in any time desired.

The inlet 5, the outlet 9 and the inlet 11 may have means for automatic control for flow in/out therethrough. As easier automation means, it is preferred that the flow in/out system from the inlet 5 to the outlet 6 and from the inlet 8 to the outlet 9 is automatically controlled so as to maintain the liquid level 4 at a constant level. In this case, the supplemental addition of a substance through the inlet 11 may be performed by manual control. In the case where the outlet 9a and the introductory part 20a are arranged at a site above the liquid level 4 and contacting the liquid level, spontaneous flowing out is possible.

The cartridge apparatus of the present invention may be pre-assembling apparatus or may be one which is assembled when needed. In the case where it is assembled when needed, the impregnation tank 1, the lid portion 2 for the impregnation tank 1, the introductory part 13 of the inlet 11, the introductory part 17 of he inlet 5, the introductory part 18 of the outlet 6, the introductory part 19 of the inlet 8, the introductory part 20 of the outlet 9, the medium 12 (may be molded together with the introductory part 13 in advance) are provided separately and connection of respective ones is achieved through taper means, for example.

As for the material of cartridge apparatus, a wide variety of known plastic materials may be used.

The preparation of the present invention enables (1) administration with high quality for a long period of time without necessitating for low temperature transportation, such as an ultra-low temperature tank for storing cell extracts for cell-free protein synthesis or using dry ice, etc. (2) By freeze-drying the cell preparation containing extracts for cell-free protein synthesis of the present invention, as it is, which was prepared by preliminarily mixing cell extracts for cell-free protein synthesis, amino acids, synthesis substrates such as ATP, and chemical substances that are indispensable for translation reaction or increase the efficiency of the reaction, such as various ions, the preparation can be readily stored or transported in the form that retains high activity of protein synthesis.

The preparation containing cell extracts for cell-free protein synthesis of the present invention does not need preparation of reaction mixture upon ex vivo protein synthesis. According to the present invention, basically addition of only water and target translation templates (mRNA) provides means for identification of gene products, synthesis thereof on a large scale, or easy analysis of translation mechanism thereof.

The present invention enables stable storage and supply of substances that are unstable at normal temperature such as substances participating in a cell-free protein synthesis reaction system, containing cell extracts for cell-free protein synthesis, other synthesis substrates exclusive of translation templates, energy sources, and chemical substances that are indispensable for translation reaction or increase the efficiency of the reaction, such as various ions, necessary for the cell-free protein synthesis system, and also enables administration of such substances with high quality for a long period of time. Provision of a freeze-dried preparation containing cell extracts for cell-free protein synthesis according to the present invention facilitates handling of cell-free protein synthesis system as compared with the conventional handling and no necessity for preparing reaction mixture shortens the operational process to improve usefulness of the cell-free protein synthesis system in industry.

Another means of the present invention utilizes the principle of molecular sieving as a carrier of a reaction tank for cell-free protein synthesis and enables a large volume cell-free protein synthesis that has been difficult to be achieved by a conventional continuous cell-free protein synthesis method using a membrane.

Further, still another means of the present invention has led to the invention of an automatic continuous protein synthesis apparatus of a dialysis type to simplify the synthesis of protein.

EXAMPLES

Hereafter, the present invention will be described in further detail by examples with reference to a preparation containing cell extracts for cell-free protein synthesis using wheat germ. However, the following examples should be construed obtaining concrete knowledge on the present invention and the scope thereof should by no means be limited by the following examples.

Example 1

(Preparation of Wheat Germ Extracts)

As the method for isolating intact germ (having capability of germination) from seeds by use of milling, floatation and sieving, the method of Johnston et al. (Johnston, F. B. et al. (1957) Nature, 179, 160-161) was used with some modification. That is, Chihoku wheat seeds (non-sterilized) produced in Hokkaido were added to a mill (Rotor Speed Mill pulverisette Type 14) in a rate of 100 g per minute and pulverized mildly at a rotation number of 8,000 rpm. The crushed seeds were pulverized again at 6,000 rpm and sieved to obtain a crude germ fraction (mesh size: 0.71 mm to 1.00 mm) and then germs having capability of germination were recovered by floatation using a mixed solution of carbon tetrachloride and cyclohexane (carbon tetrachloride:cyclohexane=2.5:1) and the organic solution was removed by drying at room temperature. Impurities such as seed coat contaminating the germ fraction was removed by adsorption using an electrified body such as a polyethylene plate.

The germ particles were classified into three fractions of small (0.71 mm to 0.85 mm), medium (0.85 mm to 1 mm), and light particle (0.85 mm to 1 mm and light in weight) respectively, using a sieve and a static electricity and finally classified visually. The small particle fraction showed the highest protein synthesis activity. As for the light particle, it is presumed that germs with a small injury caused at the pulverization underwent breakage which proceeded during the floatation. Then, to completely remove the wheat albumen component from the specimen, the wheat germs were placed in a gauze bag and washed with cool distilled water (DDW) while cooling, suspended in a 0.5% NP-40, nonionic surfactant, solution, and washed repeatedly using an ultra-sonicator until the washings were not turbid in white any longer. After ultrasonic washing once again in the presence of distilled water, wheat germs were filtered by suction and the obtained wheat germs were washed repeatedly in several times with cool distilled water (DDW) to purify the wheat germs.

The preparation of wheat germ extracts was performed in accordance with the conventional method (Erickson, A. H. et al. (1996) Methods in Enzymol., 96, 38-50). The following operation was carried out at 4° C. The purified wheat germs frozen in a liquid nitrogen were pulverized in a mortar and to the powder obtained, an extraction solution was added 1 ml/g of powder. Said solution contains 80 mM HEPES-KOH, pH 7.8, 200 mM potassium acetate, 2 mM magnesium acetate, 4 mM calcium chloride, 8 mM dithiothreitol, each 0.6 mM of 20 kinds L-amino acids, each 1 μM of FUT, E-64 and PMSF, inhibitors for proteolytic enzymes and was obtained by Patterson et al. Method, with a partial modification. The solution was stirred taking care so that no foam was generated. The supernatant obtained after centrifugation at 30,000 G for 15 minutes was recovered as germ extracts and subjected to gel filtration using a Sephadex G-25 column (Coarse) previously equilibrated with a solution (40 mM HEPES-KOH, pH 7.8, 100 mM potassium acetate, 5 mM magnesium acetate, and 4 mM dithiothreitol). The concentration of the specimen was adjusted to 170 to 250 A 260 nm (A260/A280=1.5).

The deadenylation ratio of the preparation, thus obtained was always 1% or less in plural practices in and results of 0.01 to 0.3% were obtained (the deadenylation ratio was measured according to an elimination method with aniline under acidic conditions: Endo, Y. et al. (1987) J. Biol. Chem., 262, 5908-5912, Yoshinari, S. et al. (1966) Eur. J. Biochem., 242, 585-591). The contanminants in tritin were assayed by an immunoblot method using an anti-tritin antibody, the contaminant showed below the detection limit.

Example 2

(Continuous Wheat Germ Cell-Free Protein Synthesis by a Dialysis Method)

The method for continuous wheat germ cell-free protein synthesis has been previously reported in the literature (Endo, Y. et al. (1992) J. Biotech., 25, 221-230). The reaction mixture obtained in Example 1, was charged in a Dispo Dialyzer (Spectra/Por® CE, MWCO: 25 k, volume: 0.5 ml) and the reaction was carried out at 20° C. in a dialysis system against 10 folds volume of the reaction mixture of a dialysis external liquid (20 mM HEPES-KOH, pH 7.6, 95 mM potassium acetate, 2.65 mM magnesium acetate, 4 mM dithiothreitol, 1.2 mM ATP, 0.25 mM GTP, 16 mM creatine phosphate, 0.38 mM spermidine, 20 kinds of L-type amino acids) (each 0.3 mM), 0.005% $NaN_3$, 0.05% NP-40, E-64, PMSF, each 1 mM).

Under the conditions obtained by the above method, continuous cell-free protein synthesis for wheat germ was tried and, as a result, various proteins having molecular weights ranging from 5,000 to 130,000 could be synthesized efficiently and the efficiency of synthesis was 0.3 to 1.8 mg per ml of the reaction volume (Table 1).

TABLE 1

Amount of synthesis of and properties of protein species synthesized under wheat germ cell-free system (dialysis system)

| (i) | DHFR (20 kDa) | 1.8 mg/ml (having activity) |
|---|---|---|
| (ii) | Human mitochondrial Met-tRNA synthetase (84 kDa) | 1.3 mg/ml (having no activity, antigen for preparing an antibody) |
| (iii) | Luciferase (60 kDa) | 0.7 mg/ml (having activity) |
| (iv) | Green fluorescent protein (27 kDa) | 0.4 mg/ml (having activity) |
| (v) | Human RNA helicase A (130 kDa) | 0.3 mg/ml (having no activity, an antigen for preparing an antibody) |
| (vi) | Proteasome Activator Protein α, β, and γ (28, 28, and 31 kDa, respectively) | each 0.5 mg/ml (having no activity, an antigen for preparing an antibody) |

In the above examples, the method for assaying the protein synthesis activity was performed in accordance with the method described in the previous report by Endo et al. The method for measuring the incorporation of protein into $^{14}C$-leucine, the isolation of synthesized protein by SDS-polyacrylamide gel electrophoresis and dyeing with Coomassie Brilliant Blue, and polyribosome pattern assay method by a sucrose density gradient centrifugation method were performed in accordance with the papers by Endo et al. (Endo, Y. et al. (1992) J. Biotech., 25, 221-230, Endo, Y. et al. (1975) Biochim. Biophys. Acta, 383, 305-315).

Example 3

(Forming Preparation from Wheat Germ Extracts)

The wheat germ extracts obtained by the method of Example 1, was frozen with liquid nitrogen and then water was removed therefrom in an ordinary freeze-drying apparatus (Labconc Freeze Dry System Freezone 4.5), which was operated for 3 hours. The powdery specimen thus prepared was stored in tubes by two methods, i.e., sealed in vacuum and under nitrogen gas atmosphere, respectively.

Example 4

(Confirmation for the Effect of Protein Synthesis)

The wheat germ extracts-containing preparation according to the present invention, obtained by freeze-drying and preparing by the method of Example 3 was stored at −80° C. for 2 months and separately non-freeze-dried wheat germ extracts were stored for 2 months in liquid nitrogen (−196° C.). Both wheat germ extracts were compared with each other for protein synthesis activity.

To each wheat germ extract were added 30 mM HEPES-KOH, pH 7.6, 95 mM potassium acetate, 2.65 mM magnesium acetate, 2.85 mM dithiothreitol, 0.5 mg/ml creatine kinase, 1.2 mM ATP, 0.25 mM GTP, 16 mM creatine phosphate, 0.380 mM spermidine, twenty kinds of L-type amino acids (each 0.3 mM), as a composition in accordance with a method of Erickson et al., and separately after addition of 1,000 units/ml ribonuclease inhibitor (RNasin) and NP-40 (final concentration: 0.05%), dihydrofolate reductase mRNA with a CAP (80 µg/ml of reaction volume) prepared by the method previously reported by the present inventors, (Endo, Y. et al. (1992) J. Biotech., 25, 221-230) and 50 µCi (per ml of reaction volume) of [U-$^{14}$C]-leucine (166 mCi/mmol) were added thereto. The protein synthesis activity was measured using the incorporation of [U-$^{14}$C]-leucine as a marker. The reaction was carried out at 20 to 30° C.

Figure 2:
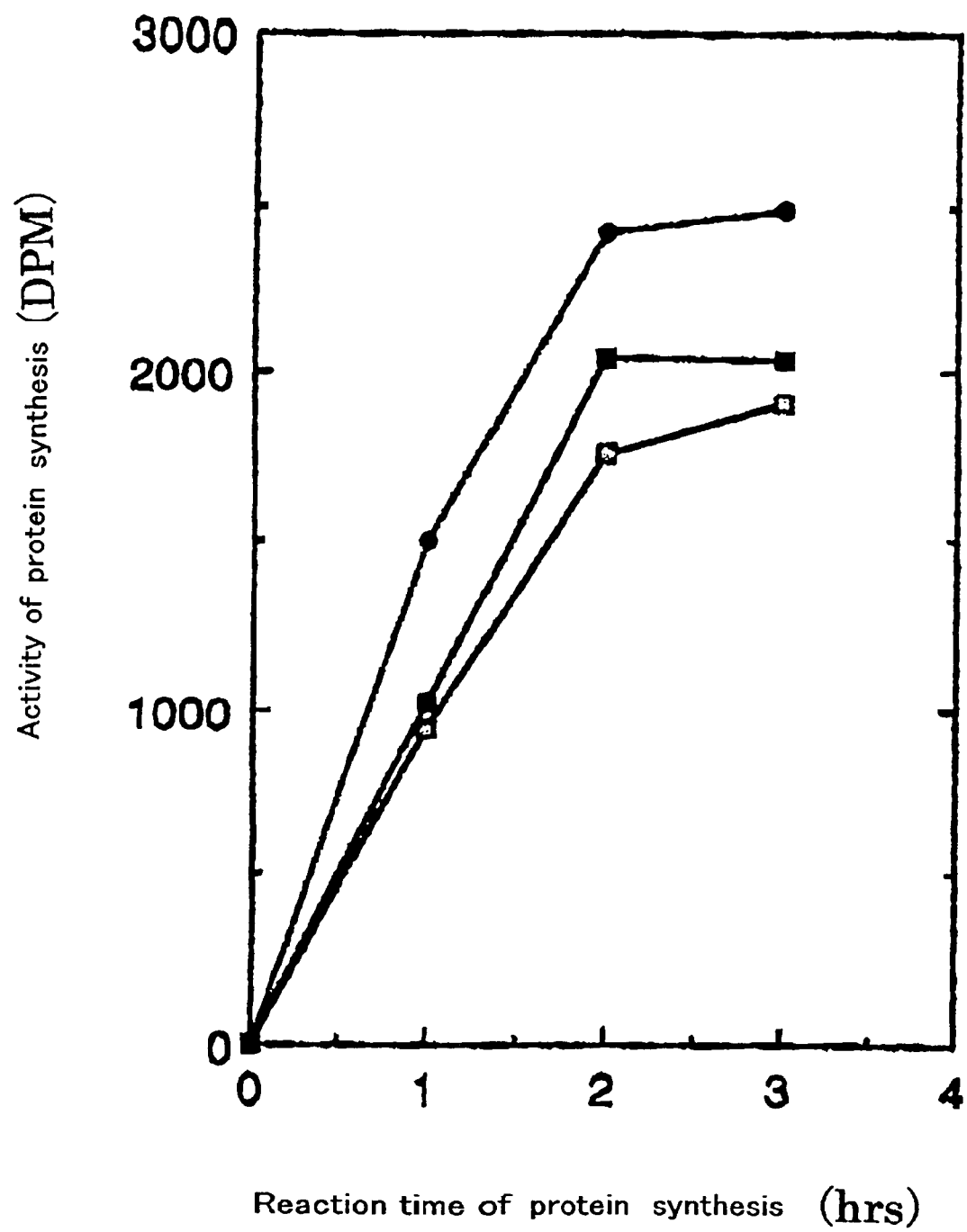
FIG. 2 shows an effect of storage temperature for freeze-dried extract on the protein synthesis activity. In the figure, symbols indicate extract stored at room temperature for 1 month as (□-□), one stored at 4° C. for the same period of time as (■-■), and one stored at −80° C. for the same period of time as (●-●), respectively.

As shown in FIG. 1, even after storage at a temperature of −80° C. for 2 months, the containing preparation (■-■) freeze-dried wheat extracts retained protein synthesis activity, equivalent to that obtained by the conventional liquid nitrogen storage (□-□). Upon study on the storage temperature after freeze-drying, comparing the protein synthesis activity after a storage period of 1 month, −80° C. (●-●) was the most stable but when stored at 4° C. (■-■) or at room temperature (□-□) the protein synthesis activity was retained sufficiently (FIG. 2).

That is, by applying the means of the present invention, the cell extracts for cell-free protein synthesis can be stored and supplied with maintaining high quality at a temperature of −80° C. to room temperature, which is higher than the conventional storage temperature.

Example 5

(Forming Preparation Containing Wheat Germ Extracts for Cell-Free Protein Synthesis)

The reaction mixture contained 20 to 60% by volume of the wheat germ extracts prepared by the method of Example 1, to which were added 30 mM HEPES-KOH, pH 7.6, 95 mM potassium acetate, 2.65 mM magnesium acetate, 2.85 mM dithiothreitol, 0.5 mg/ml creatine kinase, 1.2 mM ATP, 0.25 mM GTP, 16 mM creatine phosphate, 0.380 mM spermidine, 20 kinds of L-type amino acids (each 0.3 mM), as a composition in accordance with the method of Erickson et al. above, and then the mixture was frozen in a liquid nitrogen, followed by removing water in an ordinary freeze-drying apparatus. The powdery specimen thus prepared was stored in tubes, sealed in vacuum or under nitrogen gas atomsphere so that the components will not undergo chemical reactions.

Example 6

(Measurement of Protein Synthesis Activity)

Figure 3:
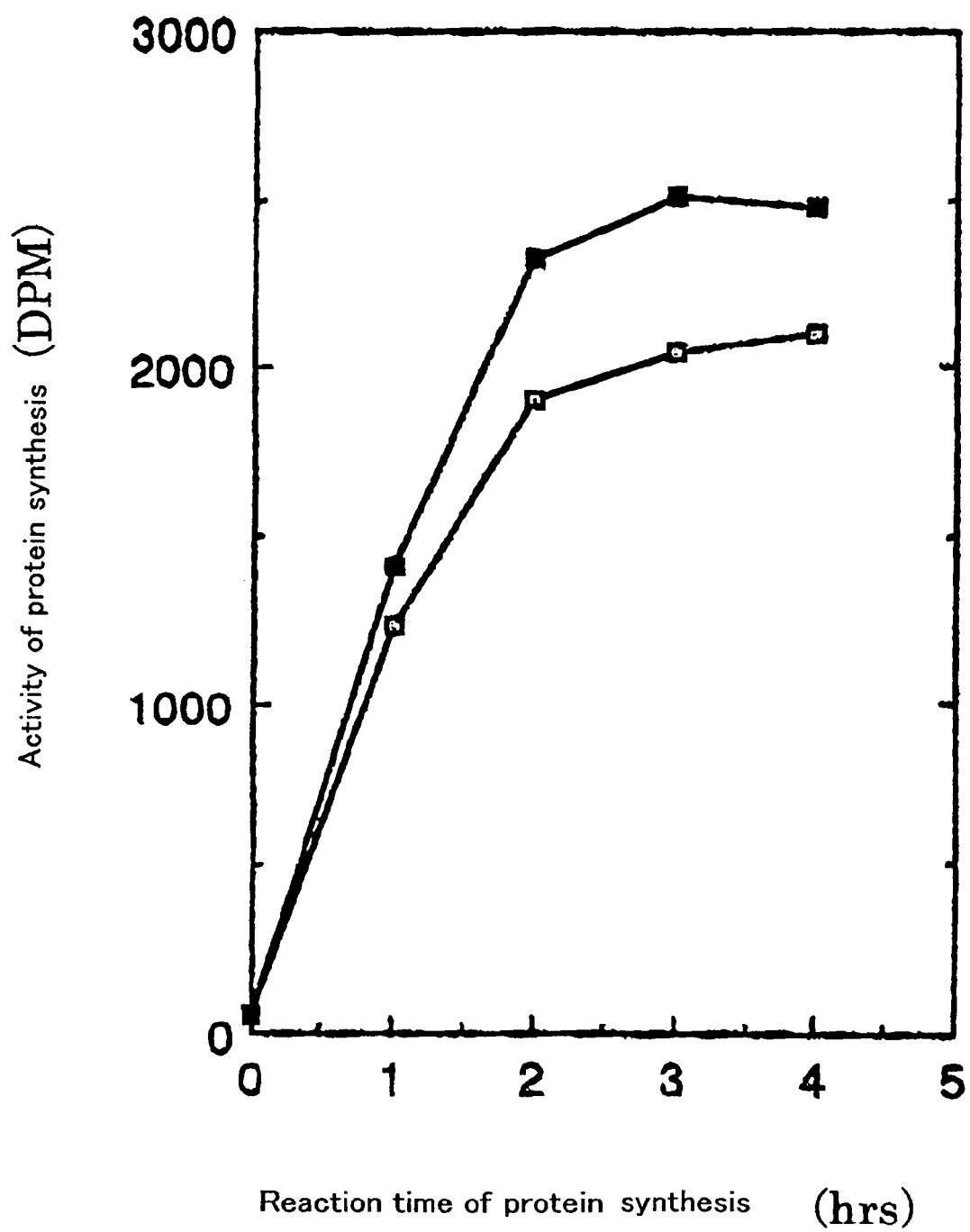
FIG. 3 shows the protein synthesis activity of synthesis solution for freeze-dried wheat germ cell-free protein in a batch reaction system. In the figure, symbols indicate extract stored in liquid nitrogen for 2 months according to a conventional method as (■-■) and one stored for the same period of time after freeze-drying as (□-□), respectively.

The preparation containing wheat germ extracts for cell-free protein synthesis prepared by the method of Example 5 according to the present invention was stored at −80° C. for 2 months and the wheat germ extracts from cell-free protein synthesis, in which the wheat germ extracts prepared by the conventional method and prepared in liquid nitrogen (−196° C.) for the same period of time as above, was added in substances having the composition prepared in accordance with a method of Erickson et al. stated in Example 5, were compared for their protein synthesis activity. After addition of 1,000 units/ml ribonuclease inhibitor (RNasin) and NP-40 (final concentration: 0.05%), the measurement of protein synthesis activity was performed by the method of Example 4. As shown in FIG. 3, the preparation containing freeze-dried wheat germ extracts for cell-free protein synthesis of the present invention (□-□) retained protein synthesis activity equivalent to that of the preparation prepared by the conventional method and stored in liquid nitrogen (■-■).

That is, by applying the means of the present invention, the preparation containing cell extracts for cell-free protein synthesis can be stored and supplied with maintaining high quality at a temperature of −80° C. to room temperature, which is higher than the conventional storage temperature, and a method for simplifying the operational process for cell-free protein synthesis system can be provided.

Example 7

(Continuous Cell-Free Protein Synthesis Using Gel Filtration Column Chromatography as a Reaction Tank: Manual Open Column Method)

After swelling Sephadex G-25 (fine) manufactured by Pharmacia AB, as a carrier for gel filtration, the column was equilibrated with a buffer solution having the composition (comprising 20 mM HEPES-KOH, pH 7.6, 95 mM potassium acetate, 2.65 mM magnesium acetate, 4 mM dithiothreitol, 1.2 mM ATP, 0.25 mM GTP, 16 mM creatine phosphate, 0.380 mM spermidine, 20 kinds of L-type amino acids (each 0.3 mM), 0.005% NaN$_3$, and 0.05% NP-40, E-64, PMSF (each 1 mM)), and packed in a column (10 mm in inner diameter, 100 mm in length:).

To this column 0.1 ml of the cell-free protein synthesis reaction solution prepared by the method of Example 1 (containing 80 μg per ml of reaction mixture of dihydrofolate reductase mRNA with 5'-CAP as a translation template) was overlaid and incubated at 23° C. for 1 hour, followed by supplying components necessary for the synthesis such as amino acids, energy sources, etc. at a flow rate of 0.5 ml per hour using a peristalic pump. After 12 hours' reaction, 1 μl of the specimen was subjected to 12.5% SDS-polyacrylamide gel electrophoresis to isolate protein, which was dyed with Coomassie Brilliant Blue and further the amount of synthesized protein was determined using a densitometer (Endo, Y. et al., (1992) J. Biotech., 25, 221-230, Endo, Y. et al., (1975) Biochim. Biophys. Acta, 383, 305-315).

The results obtained are shown in FIG. 4A. Lane 1 shows the results in the absence of templates, and Lane 3 shows the results of synthesis by a column method for 12 hours. The left-side Lane represents molecular weight markers of 94 kDa, 67 kDa, 43 kDa, 30 kDa, and 20.1 kDa, respectively from top. The arrow indicates the synthesized dihydrofolate reductase.

Example 8

(Continuous Cell-Free Protein Synthesis Using a Gel Filtration Column Chromatography as a Reaction Tank: Liquid Chromatography Apparatus)

The composition for reaction mixture, reaction method, and assay method in Example 1 were all repeated except that a column (HR 10/30, inner diameter: 10 mm, length: 300 mm) packed with Sephadex G-25 (fine) manufactured by Pharmacia AB as a carrier for gel filtration was used, a Pharmacia Biotech SMART® System liquid chromatography apparatus was utilized and the reaction volume was changed to 0.3 ml. The results obtained are shown as Lane 2 in Table 4B.

As Comparative Example, CONTINUOUS WHEAT GERM CELL-FREE PROTEIN SYNTHESIS using a dialysis method was studied. The reaction mixture for cell-free protein synthesis prepared by the method of Example 1 was charged in Dispo Dialyzer (Spectra/Por® CE, MWCO: 25 k, volume: 0.5 ml) and the reaction was carried out at 23 to 30° C. for 12 hours in a dialysis system against 10 folds the volume of the reaction mixture of a dialysis external liquid (comprising 20 mM HEPES-KOH, pH 7.6, 95 mM potassium acetate, 2.65 mM magnesium acetate, 4 mM dithiothreitol, 1.2 mM ATP, 0.25 mM GTP, 16 mM creatine phosphate, 0.380 mM spermidine, 20 kinds of L-type amino acids (each 0.3 mM), 0.005% NaN$_3$, 0.05% NP-40, E-64, PMSF, each 1 mM). The results obtained are shown Lane 2 in FIG. 4A, and Lane 1 in FIG. 4B.

Figure 4:
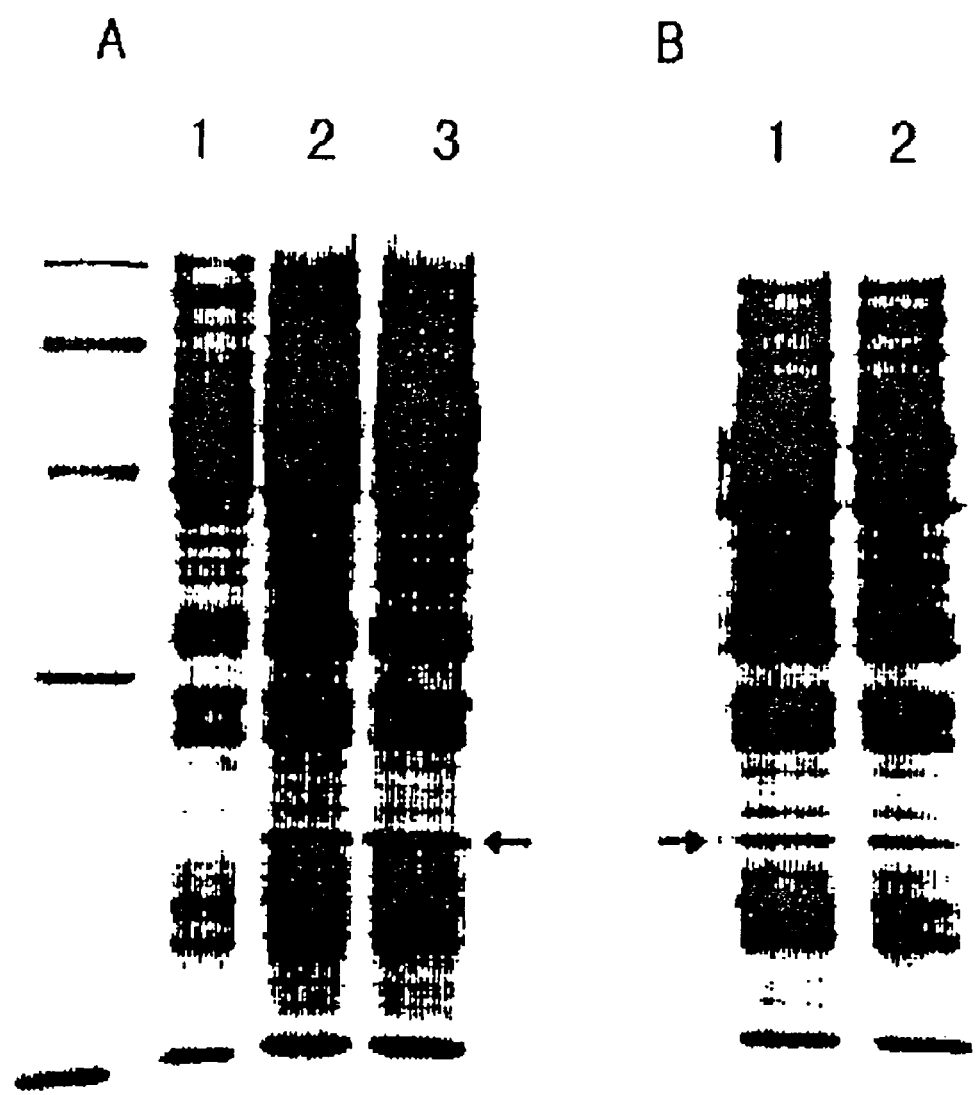
FIG. 4A is a photograph illustrating synthesizing results of cell-free protein utilizing an open column. Lane 1 shows results of absence of template and Lane 3 shows results of synthesis for 12 hours by a column method. Lane 2 shows, as a comparative example, results of synthesis for the same period of time by a continuous cell-free protein synthesis method using a conventional dialysis method.
FIG. 4B is a photograph illustrating synthesizing results of cell-free protein utilizing a commercially available liquid chromatography apparatus. Lane 1 shows, as a comparative example, results of synthesis for 12 hours by a continuous cell-free protein synthesis method using a conventional dialysis method. Lane 2 shows, as a comparative example, synthesis results for 12 hours by a continuous cell-free protein synthesis method using a conventional dialysis method. Lane 2 shows synthesis results for the same period of time by a cell-free protein synthesis method using a liquid chromatography method. Arrows indicate synthesized dihydrofolate reductase.

As shown in FIG. 4, it has been experimentally confirmed that the dehydrofolate reductase used as a model can be produced by a column method in a synthesis yield (0.25 mg/ml of reaction volume) similar to that obtained in a dialysis method either by using a manual open column method or liquid chromatography apparatus. An increase in column size enables production of protein on a large scale.

Example 9

(Improvement in the Synthesis Efficiency by Prolonging Reaction Maintenance Time by Supplemental Addition of mRNA and Creatine Kinase)

Using mRNA coding for dihydrofolate reductase as a model, synthesis reaction was performed for 24 hours. The reaction mixture contained 48% by volume of wheat germ extracts obtained in Example 1 and 1,000 units/ml ribonuclease inhibitor (RNasin), 30 mM HEPES-KOH, pH 7.6, 95 mM potassium acetate, 2.65 mM magnesium acetate, 2.85 mM dithiothreitol, 0.5 mg/ml creatine kinase, 1.2 mM ATP, 0.25 mM GTP, 16 mM creatine phosphate, 0.380 mM spermidine, twenty kinds of L-type amino acids (each 0.3 mM), 0.05% NP-40 as a composition according to the method of Erickson et al., and in addition mRNA with a CAP (80 µg/ml reaction volume), coding for dihydrofolate reductase prepared by the method already reported (Endo, Y. et al. (1992) J. Biotech., 25, 221-230).

The reaction mixture was allowed to react at 23° C. using a dialysis system against 20 folds by volume of a dialysis external liquid (containing 20 mM HEPES-KOH, pH 7.6, 95 mM potassium acetate, 2.65 mM magnesium acetate, 4 mM dithiothreitol, 1.2 mM ATP, 0.25 mM GTP, 16 mM creatine phosphate, 0.380 mM spermidine, 20 kinds of L-type amino acids (each 0.3 mM), 0.005% $NaN_3$, and 0.05% NP-40, E-64, PMSF (each 1 mM)).

After 12 hours from the initiation of the reaction, 20 µg per ml of reaction volume of mRNA with a CAP coding for dihydrofolate reductase and 200 µg per ml of reaction volume of creatine kinase were supplementally added. Separately, only 20 µg per ml of reaction volume of mRNA with a CAP coding for dihydrofolate reductase is supplementally added, or alternately only 200 µg per ml of reaction volume of creatine kinase was supplementally added. As a comparative control, the reaction was carried out without supplemental addition of either of the substances. The operation was performed manually and dialysis external liquid was not changed. The mass of synthesized protein was obtained by subjecting the obtained protein to SDS-polyacrylamide gel electrophoresis and dyeing thereof with Coomassie Brilliant Blue, measuring the intensity of the dyed band and calculating the ratio of the intensity of dyed band to that of standard preparation (Endo, Y. et al. (1992) J. Biotech., 25, 221-230, Endo, Y. et al. (1975) Biochim. Biophys. Acta, 383, 305-315).

Figure 7:
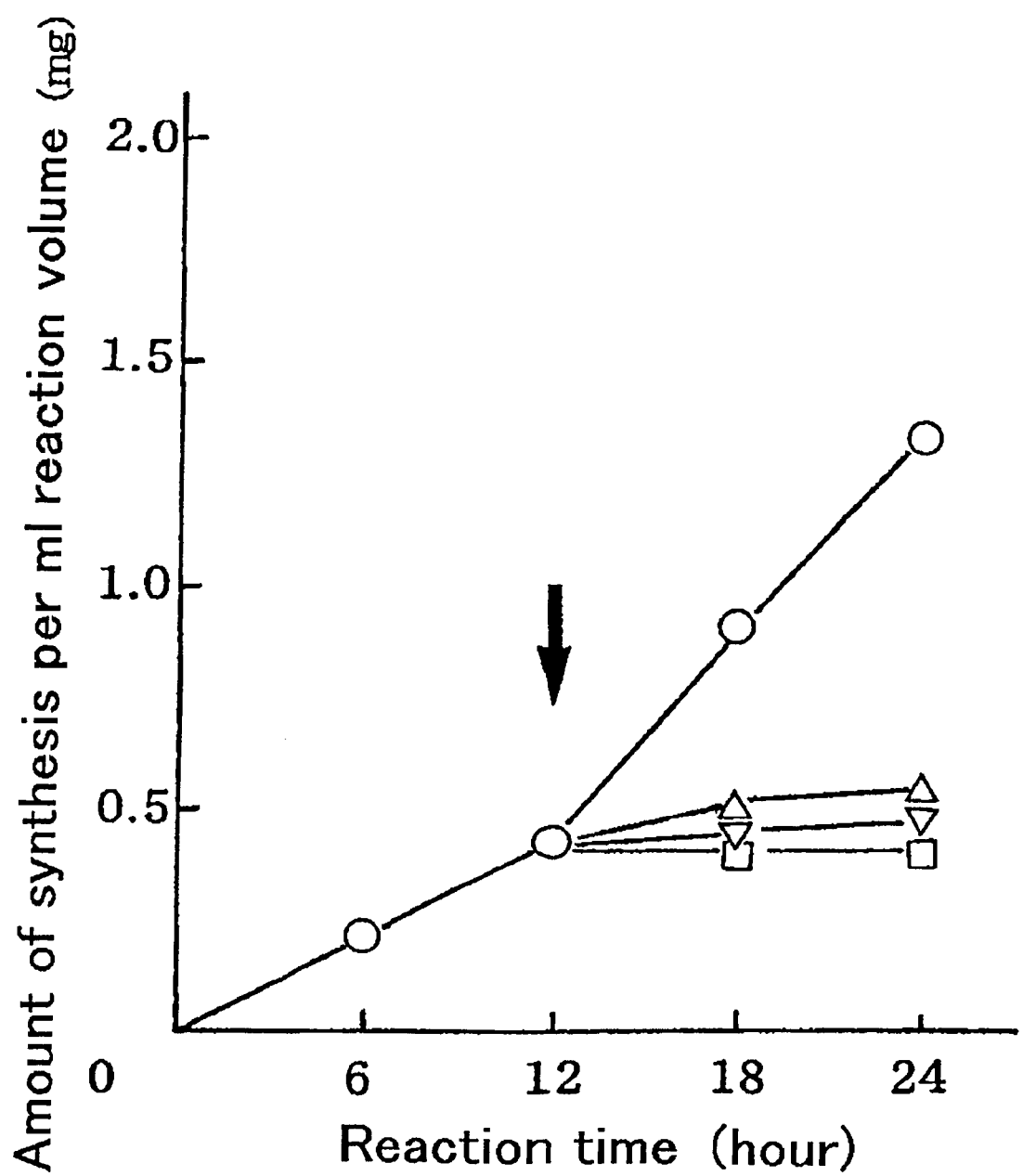

As shown in FIG. 7, it can be seen that by the supplemental addition of mRNA and creatine kinase (o-o) after 12 hours from the initiation of reaction, the reaction lasted substantially linearly. In the case of supplemental addition of either one of them (Δ-Δ) or (∇-∇), the reaction was terminated similarly to the case where no supplemental addition was made (□-□). That is, here, the above-indicated possibilities (termination of protein synthesis reaction due to a decrease in template activity of mRNA and exhaustion of energy sources resulting from a decrease in creatine kinase activity) were experimentally confirmed and a solution therefor was completed.

Example 10

(Improvement in Synthesis Efficiency for Prolonging Reaction Maintenance Time by Chronological Exchanging Dialysis External Liquid)

Protein synthesis was performed for 60 hours using mRNA coding for dihydrofolate reductase as a model by setting the conditions for composition of reaction mixture, temperature, etc. to the same as in Example 9 and the dialysis external liquid was exchanged after 24 hours and 45 hours, respectively, after the initiation of the reaction. As comparative control, protein synthesis was carried out without changing the dialysis external liquid. In either of the reaction systems, 20 µg per ml reaction volume of mRNA with a CAP coding for dihydrofolate reductase and 200 µg per ml reaction volume of creatine kinase were supplementally added. The mass of synthesized protein was measured by the method of Example 9.

Figure 8:
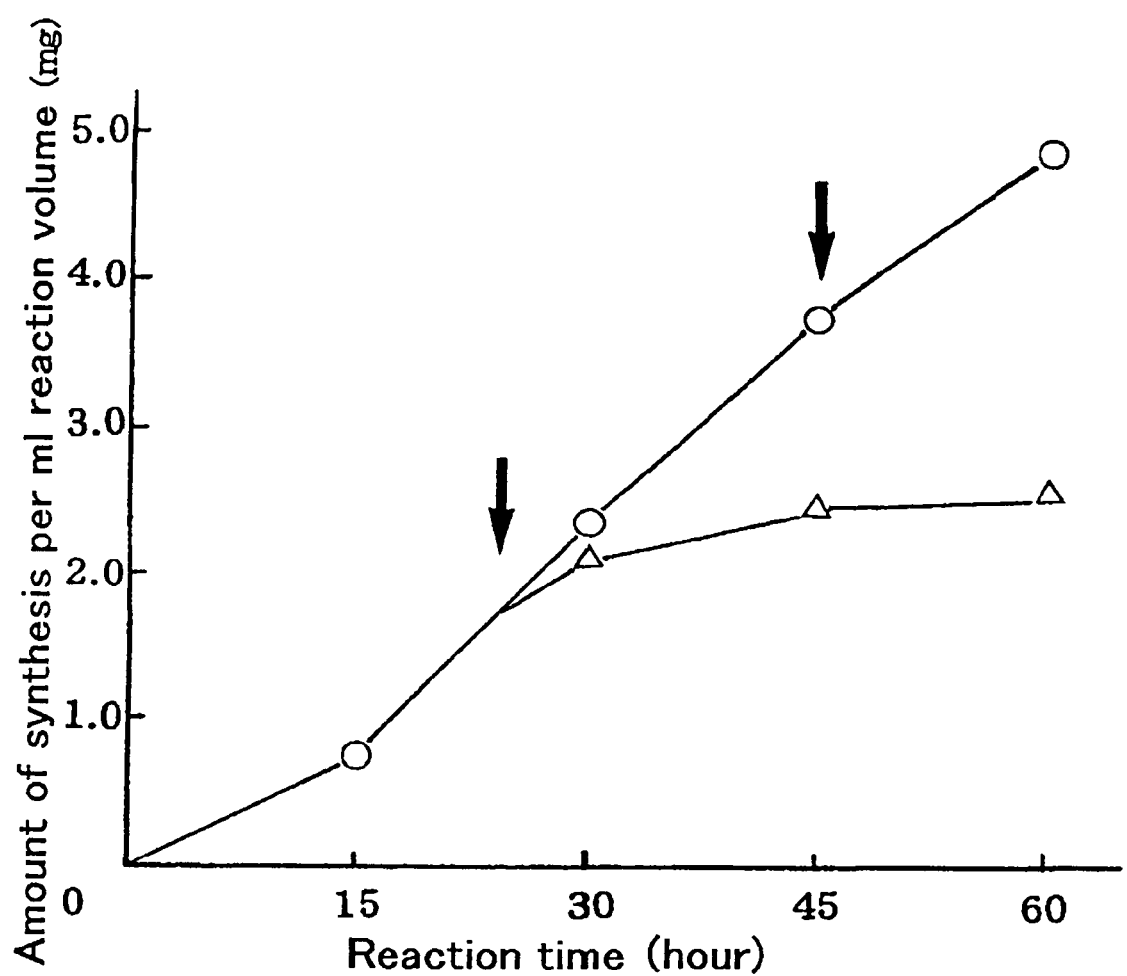
FIG. 8 shows maintenance of the effect for protein synthesis by exchange of dialysis external liquid, with ○-○ indicating that exchange of dialysis external liquid has been performed, △-△ indicating that no exchange has been performed, and arrows indicating timing of exchange.

As shown in FIG. 8, the synthesis proceeded substantially linearly without exchange of the dialysis external liquid (Δ-Δ) up until 24 hours. However, the reaction rate was decreased extremely in about 30 hours. However, the exchange of dialysis external liquid (o-o) in every 24 hours (arrows) enabled the protein synthesis to last for at least 60 hours. That is, the above-described possibilities (termination of protein synthesis reaction due to the exhaustion of raw materials essential for the protein synthesis and the accumulation of by-products) were experimentally confirmed and a method for solving them was completed.

Example 11

(Prolongation of Reaction Maintenance Time and Improvement in the Synthesis Efficiency of by Automatic Supplemental Addition of mRNA and Creatine Kinase and Automatic Exchange of a Dialysis External Liquid Using an Automatic Apparatus for Continuous Cell-Free Protein Synthesis)

Protein synthesis was performed for 60 hours using mRNA coding for dihydrofolate reductase as a model by setting the conditions of composition of reaction mixture, temperature, etc. to the same as in Example 9 and using an automatic apparatus for continuous cell-free protein synthesis. In every 12 hours after the initiation of the reaction, 20 µg per ml reaction volume of mRNA with a CAP coding for dihydrofolate reductase and 200 µg per ml reaction volume of creatine kinase each in an amount of 5 µl separately stored at 4° C. were supplementally added and allowed to react. The dialysis external liquid was supplied (0.3 ml/hour) continuously from a storage vessel maintained at 4° C. to a dialysis vessel, and discharged from the dialysis vessel at the same flow rate. After subjecting 1 µl equivalent amount, to the initial amount of reaction mixture (0.5 ml), of the reaction mixture to SDS-polyacrylamide gel electrophoresis, the protein was dyed with Coomassie Blue (FIG. 9(A)). As comparative control, the synthesis of protein was carried out in the same manner as described above after supplemental addition of only creatine kinase and without supplemental addition of mRNA with a CAP coding for dihydrofolate reductase (FIG. 9(B)). Also, to 1 µl of specimen after 0 hour from the initiation of reaction was added 1 µg of dihydrofolate reductase standard product and the electrophoresis and dyeing were performed in the same manner as described above (right side Lane in FIG. 9(A)). The amount of synthesized protein was measured by the method described in Example 9 (FIG. 9(C)).

Figure 9:
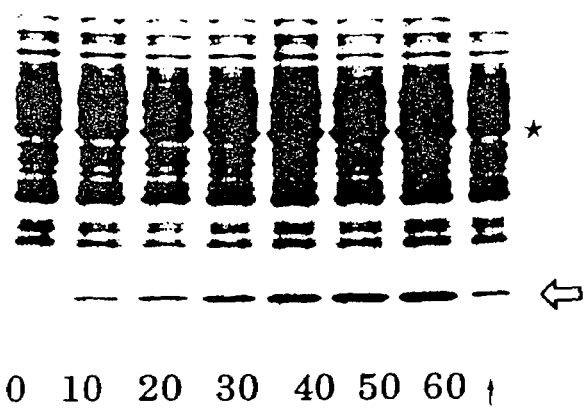
FIGS. 9A, 9B and 9C show maintenance of the effect for protein synthesis by use of an automatic apparatus. In the figure, ○-○ indicates supplemental addition of mRNA coding for dihydrofolate reductase with a CAP and creatine kinase, △-△ indicates no supplemental addition of mRNA, white arrows indicate dihydrofolate reductase, synthesis product, and symbol (★) s indicate dyed band of the supplemented creatinine kinase.
Figure 9:
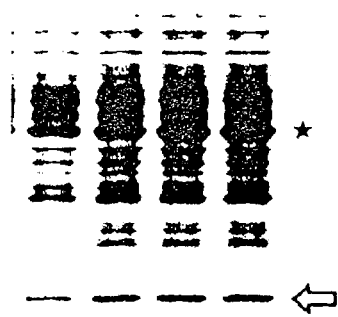
Figure 9:
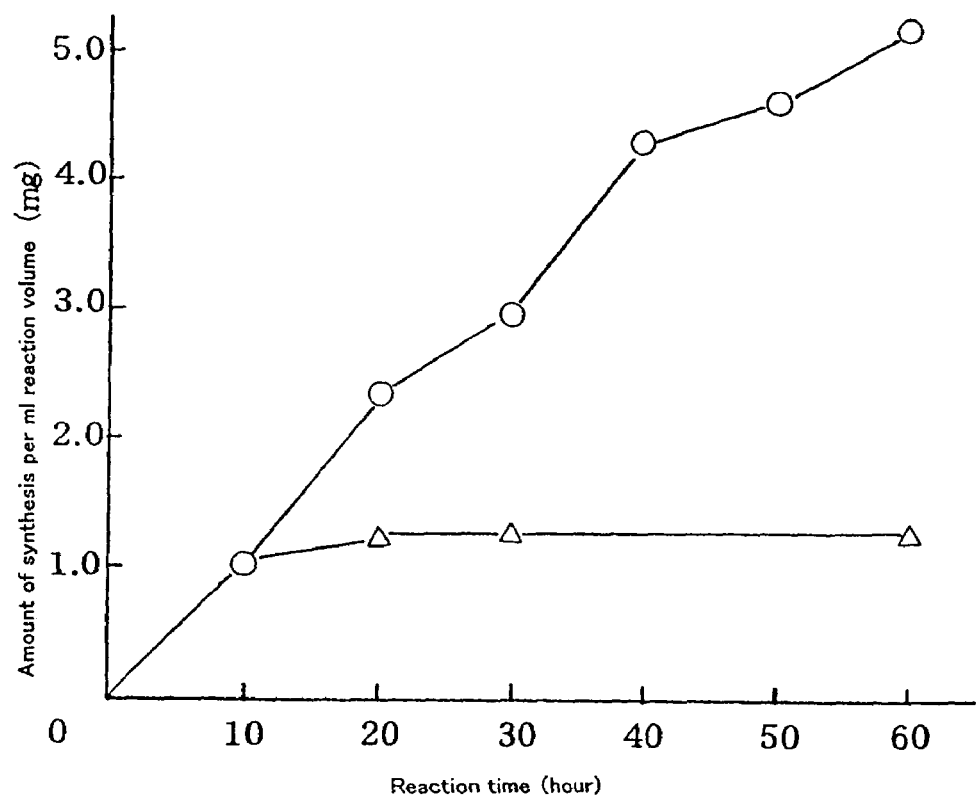

As shown in FIG. 9, in the case where no supplemental addition of mRNA with a CAP coding for dihydrofolate reductase was performed but supplemental addition of only creatine kinase was performed (Δ-Δ), the reaction was terminated in about 15 hours. Though not shown in the drawings, similar termination of reaction was observed in the case where creatine kinase was not supplemented but only mRNA with a CAP coding for dihydrofolate reductase was supplemented. On the other hand, automatic supplement of mRNA with a CAP coding for dihydrofolate reductase and of creatine kinase for every 12 hours and automatic exchange of dialysis external liquid after every 24 hours (o-o) enabled the cell-free protein synthesis to automatically proceed efficiently. That is, it was confirmed that the apparatus of the present invention functioned effectively.

What is claimed is:

1. A preparation comprising a cell extract from the germ of flowering plants for cell-free protein synthesis, wherein a ribosome deadenylation ratio of the cell extract is 1% or lower.

2. A means for cell-free protein synthesis, said means comprising:

a reaction vessel with a carrier capable of molecular sieving, and said reaction vessel storing cell extract for cell-free protein synthesis; and a material substance that participates in the cell-free protein synthesis, wherein the material substance with the carrier functions as a moving phase, and produces a product during the cell-free protein synthesis;

wherein the means is configured to add, store, exchange, discharge, or any combination thereof, the material substance, and wherein the material substance comprises at least an mRNA as a template for a protein synthesis reaction, an enzyme for an energy recycling system, a substrate, an energy source, or any combination thereof, that participates in producing protein in the cell-free protein synthesis.

3. The means for cell-free protein synthesis according to claim 2, wherein the means is configured for a continuous cell-free synthesis.

4. An apparatus for cell free protein synthesis comprising:
a structure comprising an impregnation vessel and a lid mounted to hermetically seal the vessel, wherein the structure
supports an inlet, to introduce into the apparatus, at least one material substance,
supports an outlet leading to a chamber for an outer solution for dialysis in the impregnation vessel,
supports a channel with another inlet positioned in the solution chamber in the impregnation vessel as a means for discharging metabolite,
supports an outlet leading to outside of the apparatus, and
supports a medium having a function of a dialysis membrane positioned in the solution chamber for the outer solution for dialysis in the impregnation vessel, and said medium storing cell extract from the germ of flowering plants for cell-free protein synthesis, wherein a ribosome deadenylation ratio of the cell extract is 1% or lower, wherein the material substance participates in producing protein in the cell-free protein synthesis.

5. The apparatus for cell-free protein synthesis according to claim 4, wherein the apparatus is configured for a continuous cell-free synthesis.

6. The apparatus for cell-free protein synthesis according to claim 4, wherein the material substance comprises at least an mRNA as a template for a protein synthesis reaction, an enzyme for an energy recycling system, a substrate, an energy source, or any combination thereof.

7. A means for cell-free protein synthesis, said means comprising:

a reaction vessel for dialysis and storing cell extract from the germ of flowering plants for cell-free protein synthesis, wherein a ribosome deadenylation ratio of the cell extract is 1% or lower;

a dialysis membrane; and a material substance that participates in the cell-free protein synthesis to produce a synthesized protein, wherein the synthesized protein is separated through the dialysis membrane, thereby obtaining a product, wherein the means is configured to add, store, exchange, discharge, or any combination thereof, the material substance, and wherein the material substance comprises at least an mRNA as a template for a protein synthesis reaction, an enzyme for an energy recycling system, a substrate, an energy source, or any combination thereof, that participates in producing protein in the cell-free protein synthesis.

8. The means for cell-free protein synthesis according to claim 7, wherein the means is configured for a continuous cell-free synthesis.

9. An apparatus for cell-free protein synthesis comprising:
an impregnation tank and a lid sealably fitted to the impregnation tank;
a passage having an inlet as a means for introducing at least one material substance to the impregnation tank, and an outlet communicating with a liquid chamber for a dialysis external liquid in the impregnation tank;
a passage having another inlet positioned in the liquid chamber in the impregnation tank, and configured for discharging metabolites in the dialysis external liquid, and an outlet communicating with outside of the liquid chamber, and
a medium having a function of a dialysis membrane positioned in the liquid chamber in the impregnation tank, and said medium storing cell extract from the germ of flowering plants for cell-free protein synthesis, wherein a ribosome deadenylation ratio of the cell extract is 1% or lower,
wherein the material substance participates in producing protein in the cell-free protein synthesis.

10. The apparatus for cell-free protein synthesis according to claim 9, wherein the means is configured for a continuous cell-free synthesis.

11. The apparatus for cell-free protein synthesis according to claim 9, wherein the material substance comprises at least an mRNA as a template for a protein synthesis reaction, an enzyme for an energy recycling system, a substrate, an energy source, or any combination thereof.

* * * * *